United States Patent [19]
Woodard et al.

[11] Patent Number: 5,401,515
[45] Date of Patent: Mar. 28, 1995

[54] COATED ACTIVE AGENT-CONTAINING ARTICLE

[75] Inventors: John T. Woodard; Martin C. Musolf; Patrick J. Miller, all of Midland, Mich.

[73] Assignee: Dow Corning Corporation, Midland, Mich.

[21] Appl. No.: 188,570

[22] Filed: Jan. 28, 1994

Related U.S. Application Data

[60] Division of Ser. No. 938,376, Aug. 31, 1992, Pat. No. 5,310,572, which is a division of Ser. No. 787,749, Nov. 5, 1991, abandoned, which is a continuation of Ser. No. 10,484, Feb. 3, 1987, abandoned.

[51] Int. Cl.$^6$ .................. A61K 9/32; A61K 9/36; A61K 9/58; A61K 9/62
[52] U.S. Cl. .................. 424/475; 424/459; 424/462; 424/463; 424/474; 424/482; 424/490; 424/497; 424/479; 514/770; 514/772.1
[58] Field of Search .................. 427/3; 424/475, 457, 424/468, 462, 482, 497

[56] References Cited

U.S. PATENT DOCUMENTS

| | | | |
|---|---|---|---|
| 2,983,694 | 5/1961 | Page et al. | 260/18 |
| 3,094,464 | 6/1963 | Joullie et al. | 167/82 |
| 3,509,081 | 4/1970 | Gignac et al. | 260/18 |
| 3,935,326 | 1/1976 | Groppenbacher et al. | 427/3 |
| 4,060,598 | 11/1977 | Groppenbacher et al. | 427/33 |
| 4,254,099 | 3/1981 | Asmussen et al. | 424/23 |
| 4,268,496 | 5/1981 | Ohno et al. | 424/19 |
| 4,478,819 | 10/1984 | Hercelin et al. | 424/37 |
| 4,567,231 | 1/1986 | Huebner et al. | 524/837 |
| 4,568,718 | 2/1986 | Huebner et al. | 524/837 |
| 4,584,341 | 4/1986 | Huebner et al. | 524/837 |
| 4,618,645 | 10/1986 | Bauman et al. | 524/745 |
| 4,698,264 | 10/1987 | Steinke | 428/402.2 |
| 4,716,041 | 12/1987 | Kjornaes et al. | 424/468 |
| 4,781,858 | 11/1988 | Mizukami et al. | 252/315.2 |
| 4,806,337 | 2/1989 | Snipes et al. | 71/65 |

FOREIGN PATENT DOCUMENTS 171457  2/1986  European Pat. Off. .

Primary Examiner—Thurman K. Page
Assistant Examiner—James M. Spear
Attorney, Agent, or Firm—Marshall O'Toole Gerstein Murray & Borun

[57] ABSTRACT

Aqueous coating compositions for forming elastomeric films around active cores (e.g., drugs) comprising a dispersion of pre-crosslinked polyorganosiloxane latex particles, colloidal silica particles, and a water-dispersible organic material (e.g., polyethylene glycol) are disclosed and claimed. The elastomeric films formed by the coating compositions are used to control the rate of release of an active agent in the cores into an aqueous environment. Methods of formulating the coating compositions and active cores coated with the coating compositions are also disclosed.

14 Claims, 7 Drawing Sheets

COATED ACTIVE AGENT-CONTAINING ARTICLE

CROSS-REFERENCE TO RELATED APPLICATIONS

This is a division of commonly assigned application Ser. No. 07/938,376, filed Aug. 31, 1992, now U.S. Pat. No. 5,310,572, which is a division of application Ser. No. 07/787,749, filed Nov. 5, 1991, now abandoned, which is a continuation of application Ser. No. 07/101,484, filed Feb. 3, 1987, now abandoned.

BACKGROUND OF THE INVENTION

The present invention relates generally to aqueous compositions which can be coated on active cores (e.g., pharmaceutical preparations, herbicides, chemical reactants, etc.) to provide for the controlled release of an active agent over a period of time. These aqueous coating compositions contain non-toxic materials—a pre-crosslinked polyorganosiloxane, colloidal silica and a water-dispersible organic polymer—which can be coated or sprayed onto active substrates, including water-soluble substrates and dried to form an elastomeric film. Upon exposure to an aqueous environment, the coated substrates of the present invention respond in a manner which causes the active agent to pass into the aqueous surroundings at a substantially constant rate.

Conventional tablets dissolve at a non-uniform rate characterized by an initial rapid introduction of the active ingredient into its surroundings, followed by a relatively low rate of release. Efforts to provide for a more uniform administration of an active agent has prompted the use of sustained-release compositions which employ granules of active ingredients coated with differing thicknesses of cellulose acetate/polyethylene oxide solutions. Controlled release is achieved by collecting granules of varying coating thicknesses into a single capsule.

Another approach of particular interest to the present invention is illustrated in U.S. Pat. No. 4,268,496. The foregoing patent discloses pharmaceutical compositions coated with two-component, aqueous coating compositions comprising water-soluble cellulose derivatives and curable organopolysiloxane or organohydrogenpolysiloxane polymers. The coating compositions disclosed in this patent do not use a reinforcing colloidal silica filler and the patent teaches that organometallic or platinum catalysts can be employed, if necessary, to cure the siloxane polymer.

U.S. Pat. No. 3,935,326 discloses water-based synthetic resins for spraying on tablet cores. The patent describes both the use of water-soluble substances, including polyethylene glycols, and the possibility of employing highly dispersed silicic acid fillers in the spraying compositions. The resin components disclosed are not silicones, but comprise organic resins which are formed from free radical emulsion polymerizations, are not crosslinked, and require the addition of plasticizers.

European Patent Application 0 171 457 discloses tablet coating compositions comprising a water-dispersible material (e.g., polyethylene glycol) and a semipermeable membrane. The published application indicates that polydialkylsiloxanes can be used to form such membranes, but teaches that the membrane is formed by dispersing the membrane precursor in an organic solvent.

SUMMARY OF THE INVENTION

The coating compositions of the present invention are aqueous dispersions which, when applied to a substrate and the water is removed, form tough, elastomeric films which allow the migration of an active agent through the film without rupture. As a consequence, drugs or other active agents which are coated with the compositions of the present invention have a number of advantages: 1) the coating results in substantially zero order release of the active agent into a surrounding aqueous environment (i.e., release at a constant rate); 2) the coating is elastomeric and provides sufficient tensile strength and elongation so that it can expand in an aqueous environment, such as the stomach, without rupture; 3) notwithstanding its elastomeric nature, the coating is formed from an emulsion which contains no curing or crosslinking agents which could cause adverse toxicological effects, and is likewise free of organic initiator residues such as would be present with free radical polymerizations; 4) the coating is formed on the active substrate utilizing conventional coating techniques (including conventional tablet coating equipment); and, 5) notwithstanding the fact that the coating compositions are themselves aqueous, conventional water-soluble cores (e.g., tablets) can be coated with no deleterious effects.

The coating compositions of the present invention are aqueous dispersions which contain three essential ingredients:

A) a latex of crosslinked polydiorganosiloxane which is substantially free from metal or organometallic catalysts;
B) colloidal silica; and
C) a water-dispersible organic material containing oxa-or oxo- functionality.

Methods of preparing the aqueous, crosslinked polydiorganosiloxane latex component of the present invention are described by Huebner and Saam in U.S. Pat. No. 4,568,718, which issued Feb. 4, 1986, and in U.S. Pat. No. 4,584,341 which issued Apr. 22, 1986. These patents disclose metallic-catalyst-free aqueous latices formed from the reaction of an oil-in-water emulsion of a hydroxyl endblocked polydiorganosiloxane fluid with an alkoxysilicon cross-linker (e.g., an orthosilicate, a polysilicate, or an alkyltrialkoxysilane). These compositions also contain an anionic, surface active compound which serves both as a surfactant for dispersing the polydiorganosiloxane in water and as a catalyst in the cross-linking reaction.

The hydroxyl endblocked polydiorganosiloxane can be any of the polydiorganosiloxanes endblocked with hydroxyl radicals and can be represented by the formula

where each R is selected from the group consisting of methyl, ethyl, propyl, phenyl, vinyl, alkyl, and 3,3,3-trifluoropropyl, and mixtures thereof wherein at least 50 percent of the radicals are methyl radicals. The polydiorganosiloxane can be a homopolymer with the same kind of repeating diorganosiloxane units or it can be a combination of two or more kinds of repeating diorganosiloxane units, such as combination of dimethylsiloxane units and methylphenylsiloxane units. The polydiorganosiloxane can also be a mixture of two or more kinds of polydiorganosiloxanes. The polydiorganosiloxanes are those in which x has an average value in the range of from 3 to 100 inclusive. The preferred polydiorganosiloxanes are those in which x is at least large enough that the viscosity of the polydiorganosiloxane is at least 0.05 Pa's at 25° C. (x is about 25). A preferred polydiorganosiloxane is a polydimethylsiloxane having a viscosity of from about 0.05 Pa's to 0.15 Pa's at 25° C., the value of x for such a material being from about 25 to 80.

The alkoxysilicon compound has the formula $$R_a'Si(OR^3)_{4-a}$$

where R' is a monovalent hydrocarbon radical having up to 12 carbon atoms, $R^3$ is an alkyl radical having from 1 to 6 inclusive carbon atoms, and a is 0 or 1; a partial hydrolyzate of the silane where the partial hydrolyzate is soluble is the polydiorganosiloxane; and mixtures of silane and partial hydrolyzate. These alkoxy silicon compounds are well known in the art and many are commercially available. R' can be illustrated by radicals such as methyl, ethyl, propyl, isopropyl, butyl, hexyl, dodecyl, vinyl, allyl, phenyl, tolyl, and 3,3,3-trifluoropropyl. $R^3$ is an alkyl radical such as methyl, ethyl, propyl, and hexyl. Preferably both R' and $R^3$ are methyl and/or ethyl. Preferred silanes include methyltrimethoxysilane, ethyltrimethoxysilane, methyltriethoxysilane, ethyltriethoxysilane and ethylorthosilicate with ethylorthosilicate most preferred. A preferred partial hydrolyzate of silane is ethylpolysilicate.

The amount of alkoxy silicon compound present can vary from 0.5 to 15 parts by weight based upon 100 parts by weight of the hydroxyl endblocked polydiorganosiloxane with a preferred amount of from 1 to 5 parts by weight. The amount of alkoxy silicon compound used has an effect upon the degree of cross-linking in the emulsion polymer. The preferred amount of alkoxy silicon compound is dependent upon the hydroxyl endblocked polydiorganosiloxane used, the alkoxy silicon compound used, the time allowed for reaction, and the type and amount of surface active anionic catalyst. The preferred amount of alkoxy silicon compound is determined by the user's physical property requirements, in particular, how much elongation is desired in the elastomer produced, and what are acceptable tensile strength values. Higher amounts of alkoxy silicon compound cause more crosslinking so that the elongation at break of the elastomer is lowered.

A surface active anionic component is used to form the emulsion and to catalyze the reaction of the hydroxyl endblocked polydiorganosiloxane and the alkoxy silicon compound. The surface active anionic component (surfactant) is preferably selected from the group consisting of alkyl aromatic sulfonic acids and hydrogen alkyl sulfates. Especially preferred are dodecylbenzene sulfonic acid and hydrogen lauryl sulfate.

The surface active anionic component performs a dual -function. The anionic component must serve as a surfactant so that the hydroxyl endblocked polydiorganosiloxane is properly emulsified to form the oil-in-water emulsion. In such an emulsion, the surfactant forms a layer over the surface of the polydiorganosiloxane particles and keeps them from coalescing. The surfactant on the surface of the particles also acts as a catalyst in the crosslinking reaction between the hydroxyl end-blocked polydiorganosiloxane and the alkoxy silicon compound.

Dodecylbenzene sulfonic acid is available commercially. Hydrogen lauryl sulfate may be obtained by dissolving sodium lauryl sulfate in water, then adding hydrogen chloride to form the hydrogen lauryl sulfate and sodium chloride. Another method treats the sodium lauryl sulfate solution with a cation exchange resin which exchanges sodium ion for hydrogen ion. The solution of hydrogen lauryl sulfate is then used as the catalyst in the method of this invention. The hydrogen lauryl sulfate can also be produced in situ by homogenizing polydiorganosiloxane and water with sodium lauryl sulfate, then adding hydrogen chloride to the emulsion formed by the homogenization to convert the sodium lauryl sulfate to hydrogen lauryl sulfate catalyst.

The latex can be formed by homogenizing a mixture consisting essentially of the above-described polydiorganosiloxane, from 15 to 75 millimoles of anionic surfactant, and water to yield an oil-in-water emulsion; that is, an emulsion of particles of polydiorganosiloxane dispersed in water. The amount of water used should be sufficient to allow the formation of an oil-in-water emulsion. Generally, water should constitute between 20 and 80% by weight of the total emulsion. Water contents between 35 and 65 percent by weight are preferred (approximately 50 to 200 parts by weight based on 100 parts of polydiorganosiloxane polymer). The emulsions can be prepared by any of the well known processes for making emulsions such as in a high shear mixer or homogenizer. The emulsion particle size is dependent upon the method of emulsification used and on the level of surfactant. Typically particles have an average diameter of about 225 nanometers.

After the polydiorganosiloxane/anionic surfactant mixture has been homogenized to form an emulsion, from 0.5 to 15 parts by weight of alkoxy silicon compound is mixed into the emulsion to provide a multifunctional unit which reacts with the hydroxyl endblocked polydiorganosiloxane to crosslink the polymer. The preferred amount of alkoxy silicon compound is dependent upon the particular alkoxy silicon compound used and upon the amount of crosslinking desired in the emulsion particles. Higher amounts of alkoxy silicon compound results in more crosslinking.

After addition of the alkoxy silicon compound, the emulsion can be maintained at a temperature of from 15° to 30° C., preferably at room temperature, until the desired amount of crosslinking is achieved. At room temperature conditions, the crosslinking reaction takes at least 5 hours, typically from 7 to 20 hours. The preferred holding time, at this temperature, is at least 12 hours, since the amount of cross-linked product does not markedly increase after that point. The reaction is believed to comprise a chain extension initially, then a combination of polymerization and crosslinking to yield particles of higher molecular weight crosslinked polymer. The crosslinking reaction requires acid conditions, preferably a pH of less than about 5. Use of one of the preferred anionic surfactants will result in an acid mixture having a pH of less than 2.

An alternative approach for formulating the cross-linked polydiorganosiloxane latex component is to form a non-solvent-containing solution by dissolving the alkoxysilicon crosslinker in the hydroxyl end-blocked siloxane and adding this non-aqueous solution to a solution of neutral anionic surfactant in water. High speed mixing will serve to completely disperse the system. Thereafter the system can be acidified to initiate the cross-linking reaction.

No matter which approach is utilized to form the crosslinked polyorganosiloxane latex, the crosslinking reaction can be terminated by neutralizing the system with a base. Although any water-soluble basic material can be employed, the use of ammonium hydroxide is preferred since it does not introduce a metal cation into the coating composition.

The foregoing Huebner and Saam patents also disclose that the crosslinked polyorganosiloxane latex can be reinforced by adding a colloidal silica sol. Colloidal silica sols are commercially-available dispersions of colloidal silica in water having a pH range of from about 3.2 to about 10.5. They are available at concentrations of colloidal silica varying from 15 percent to 50 percent by weight, with average particle sizes varying from about 4 to 60 nanometers. Basic colloidal silica sols (pH 9.0–11.0) manufactured by the Nalco Chemical Company under the product designations 1115, 2326, 1130, 1140 and 1050, have been found to provide acceptable coatings when incorporated into the compositions of the present invention.

The preferred amounts of colloidal silica employed in the coating compositions of the present invention are from 5 to 50 parts by weight per 100 parts of polyorganosiloxane latex (dry basis). The optimum level will depend on the type and amount of water-soluble polymer and the desired release rate of the active agent.

The third essential component for use in the coating compositions of the present invention is a water-dispersible organic material containing oxa- or oxo- functionality. These materials enhance the movement of active agent across the elastomeric barrier formed by the reinforced silicone elastomer component. Examples of such organic materials include polyvinylpyrrollidone, poly(alkylene glycols), esters and polyesters of poly(alkylene glycols), polyhydric alcohols, and esters and polyesters of polyhydric alcohols. Oligosaccharides such as sucrose, fructose and maltodextrins can also be employed. Polyethylene glycols having a molecular weight between 400 and 8000 are especially preferred.

Increasing the amount of polyethylene glycol (PEG) in a coating composition results in faster release of the active agent from cores which have been coated with such composition. For example, a nearly 7 fold increase in release rate was observed when the percentage of PEG 6000 was increased from 20.0 to 30.0, and a 3 fold increase resulted when the percentage was increased from 30.0 to 40.0.

This effect is less pronounced for lower molecular weight organic polymers. Thus, although an increase in the percentage of PEG 400 or PEG 1540 in coating compositions which are formulated in accordance with the present invention results in faster release rates, the effect is much less dramatic than that with the higher molecular weight PEG 6000.

Satisfactory coatings have been formulated utilizing as little as 8 parts by weight of PEG per 100 parts by weight of silicone latex particles. Increased levels of PEG in the coating composition weakens the coating film when the coated substrates are immersed in water. Coating rupture was observed for substrates coated with compositions containing 50.0% PEG, regardless of the molecular weight of the PEG utilized.

The coating compositions can be applied to active cores (e.g., tablets, prills or beads) by conventional coating or spraying techniques, utilizing conventional pan systems, perforated pan systems (e.g., a Glatt coater, manufactured by Glatt Air Techniques, Inc., Ramsey, N.J.), or fluidized bed (air support) systems. If spray-coated, the coating composition can be applied by employing either high-pressure, airless or low-pressure, air-atomized spraying equipment. The viscosity of the composition can be adjusted by controlling the water content, in light of the application procedure selected. It is generally desirable to employ the minimum amount of water which can be tolerated by the application procedure in order to lessen drying times and to prevent degradation of the water-soluble cores. No matter how applied, the particles contained in the coating composition will coalesce to form an elastomeric film, upon drying.

Film thickeners will affect the release characteristic of the active core. In general, release is inversely proportional to the thickness of the applied coating. However, the coating should be thick enough to not rupture when exposed to moisture.

It is theorized that the release of an active agent from coated substrates which have been exposed to an aqueous environment follows the following pathway:
1) Penetration of the aqueous dissolution medium into the coating film;
2) Leaching out of the organic, water-soluble polymer (e.g., PEG) from the coating with concurrent hydration and swelling of the coating;
3) Dissolution of the active agent in the coated core or substrate in the penetrant water with a concomitant increase in osmotic pressure inside the coating; and
4) Diffusion of the dissolved active agent through the porous, hydrated and swollen coating film.

Figure 1:
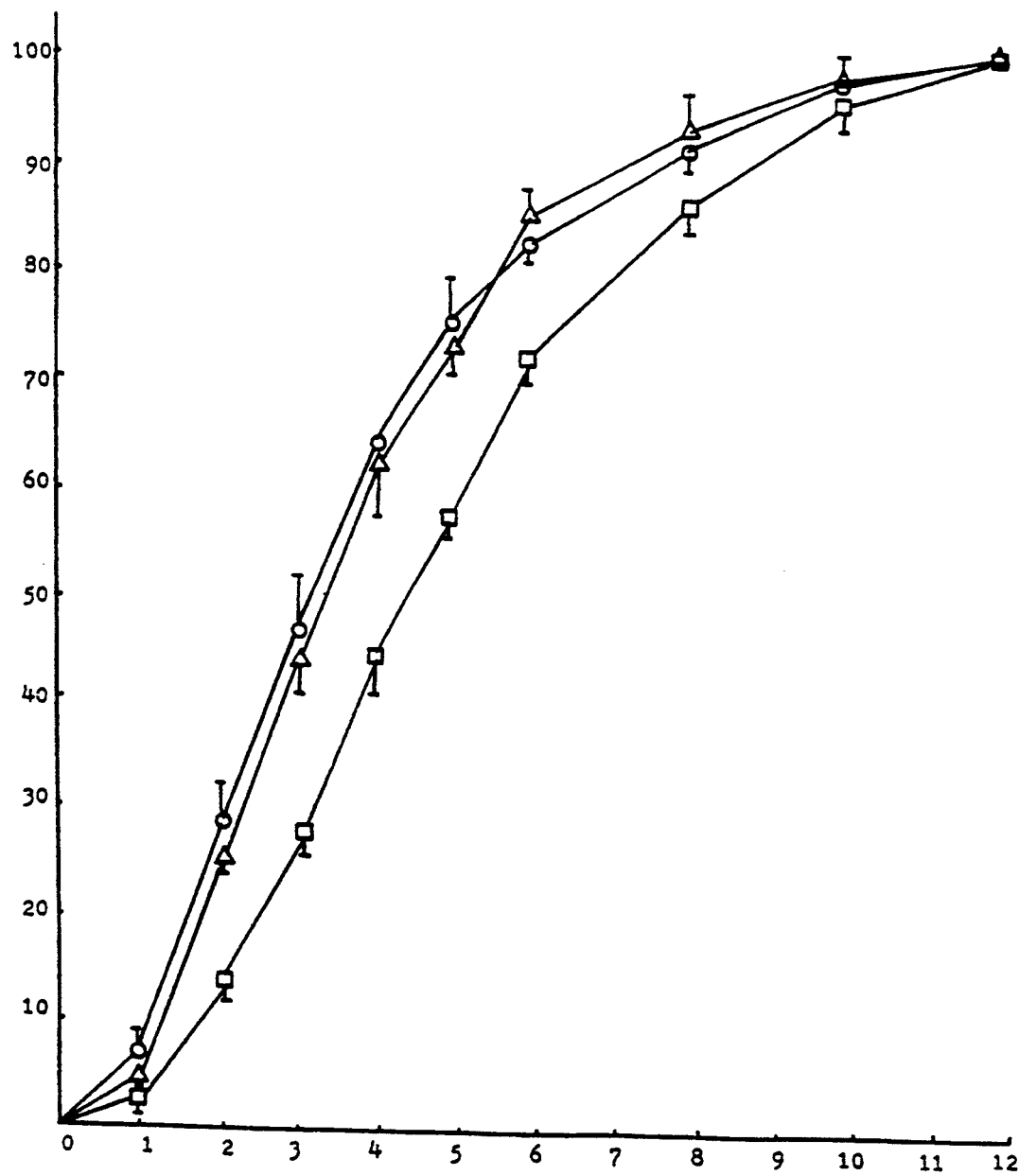
FIG. 1 is a graph which depicts the release of ascorbic acid from beads which have been coated with an aqueous coating composition which has been formulated in accordance with the teachings of the present invention. Details concerning the coating composition and the procedures utilized to generate the data which is illustrated can be found in Example II.

The following examples are presented for purposes of illustration and should not be construed as limiting the invention which is delineated in the claims. Accordingly, although the data presented in the examples relates to coated pharmaceutical compositions (a preferred active core), the coating compositions can be deposited on other substrate cores for the release of insecticides, herbicides, pheromones or chemical reactants, to name but a few possible applications.

EXAMPLE I

Preparation of Base Polyorganosiloxane Latex

A non-solvated mixture of 100 parts by weight of hydroxyl endblocked polydimethylsiloxane fluid having a viscosity of about 0.09 Pa's at 25° C. and about 4.5 parts by weight of ethylorthosilicate was formed and the mixture was agitated thoroughly until homogenous.

A second, aqueous solution was prepared by gradually adding 8.67 parts of an aqueous concentrate of sodium lauryl sulfate (Duponal* WAQE—a 30 wt % solution of sodium lauryl sulfate in H2O) to 66.5 parts by weight of distilled water in order to form a dilute, aqueous anionic-surfactant-containing solution containing 2.6 parts by weight of sodium lauryl sulfate and 72.5 parts by weight of distilled water. Care was taken in performing the dillution step in order to avoid excessive foaming.
* A trademark of E. I. dupont deNemours & Company.

The first, non-aqueous, silicone mixture was dispersed in the second aqueous solution with mild agitation and then passed through a laboratory homogenizer at a pressure of 7800 p.s.i. Although the resultant emulsion appeared stable, the homogenization process was repeated to ensure that a uniform stable, oil-in-water emulsion had been formed.

Eight (8) parts by weight of Dowex ** HCR-W-2-H, an ion exchange resin, was added to the emulsion in order to generate hydrogen lauryl sulfate, in situ, and the mixture was permitted to stand at room temperature for two hours. The mixture was filtered to remove the solid ion exchange resin, and the pH of the emulsion was measured and found to be less than 2.0. The emulsion was maintained at room temperature for an additional ten hours and thereafter neutralized with 0.5N ammonium hydroxide.
** A trademark of The Dow Chemical Company.

EXAMPLE II

Preparation of Coating Dispersion

The base polyorganosiloxane latex of Example I (approximately 53% solids) was utilized to formulate two PEG-containing coating formulations—Dispersion A and Dispersion B—having the compositions shown in Table 1. Dispersion A contained a 50:50 mixture of both a high molecular weight polyethylene glycol, PEG 6000, and a low molecular weigh material, PEG 400. Dispersion B contained the lower molecular weight PEG 400 only.

The dispersions were formed by first diluting the latex with water and thereafter adding the indicated weight of colloidal silica to the diluted latex dispersion with the aid of a high-shear mixer. After thorough shear-mixing, a predetermined weight of PEG 400 and/or PEG 6000 was added to the dispersion, and the mixture was stirred, using a propeller stirrer. After thorough mixing, the resultant coating composition was filtered through a stainless steel 100-mesh screen into glass bottles.

Coating Dispersions A and B were used to coat both ascorbic acid beads and phenylpropanolamine hydrochloride beads. The beads employed were approximately spherical in shape and had a diameter of about 1 millimeter. Each ascorbic acid bead contained approximately 80% active drug, and each phenylpropanolamine hydrochloride bead contained approximately 70% drug. The bead coating operation was performed in a Glatt tower within 24 hours of the preparation of the Coating Dispersions. Approximately one hour was required to coat one kilogram of beads with 400–500 grams of coating dispersion.

TABLE 1

Preparation of two silicone coating dispersions incorporating colloidal silica, water and Polyethylene glycols.

| Components | Weight (Gms) | Solids (Gms) | (w/w) % Solids |
|---|---|---|---|
| Dispersion A | | | |
| Crosslinked polydimethylsiloxane polymer dispersion * | 175 | 92 | 72 |
| Colloidal silica dispersion ** | 135 | 23 | 18 |
| PEG 400 | 6.4 | 6.4 | 5 |
| PEG 6000 | 6.4 | 6.4 | 5 |
| Deionized water | 77 | — | — |
| Total | 400 | 128 | 100 (32) *** |
| Dispersion B | | | |
| Crosslinked polymer dispersion * | 188 | 100 | 74.5 |
| Colloidal silica dispersion | 141 | 24 | 18 |
| PEG 400 | 10 | 10 | 7.5 |
| Deionized water | 161 | — | — |
| Total | 500 | 134 | 100 (27) *** |

* Formulated in accordance with Example I
** Nalco 1115 - a 17% dispersion of colloidal silica in water, having a mean particle size of 4 nanometers and a pH of 10.4
*** Percent solids in coating dispersion The coated beads were placed in aqueous environments and periodically sampled and analyzed by spectrophotometric means. In the case of the coated phenylpropanolamine hydrochloride samples, the chloride ion was also assayed by titration.

Ion Selective Potentiometric Assay for Chloride Ions

The chloride ion concentration in phenylpropanolamine hydrochloride solution was determined using a chloride ion selective electrode (Orion, model 94–17B)

and a reference electrode in conjunction with a specific ion meter (Orion, model 407). A standard curve was prepared by plotting the meter voltage versus the logarithms of the chloride ion concentration of a phenylpropanolamine hydrochloride solution from $2.5 \times 10^{-7}$M to $4.2 \times 10^{-6}$M.

Spectrophotometric Assay for Phenylpropanolamine Cation

The wavelength used for the assay was 260 nm. Measurements were carried out using a Perkin-Elmer spectrophotometer (Model 111-055) and 1 cm pathlength quartz cuvettes. A previously constructed Beer's Law plot was used to calculate the concentration of phenylpropanolamine in solutions where the phenylpropanolamine concentration ranged from 50 ug/ml to 800 ug/ml.

Ascorbic Acid Assay Methodology

Ascorbic acid concentrations were determined by spectrophotometry using wavelength of 270 nm. A previously constructed Beer's Law plot was used to calculate the concentration of ascorbic acid in solutions where the ascorbic acid concentration ranged from 5 ug/ml to 30 ug/ml.

Figure 2:
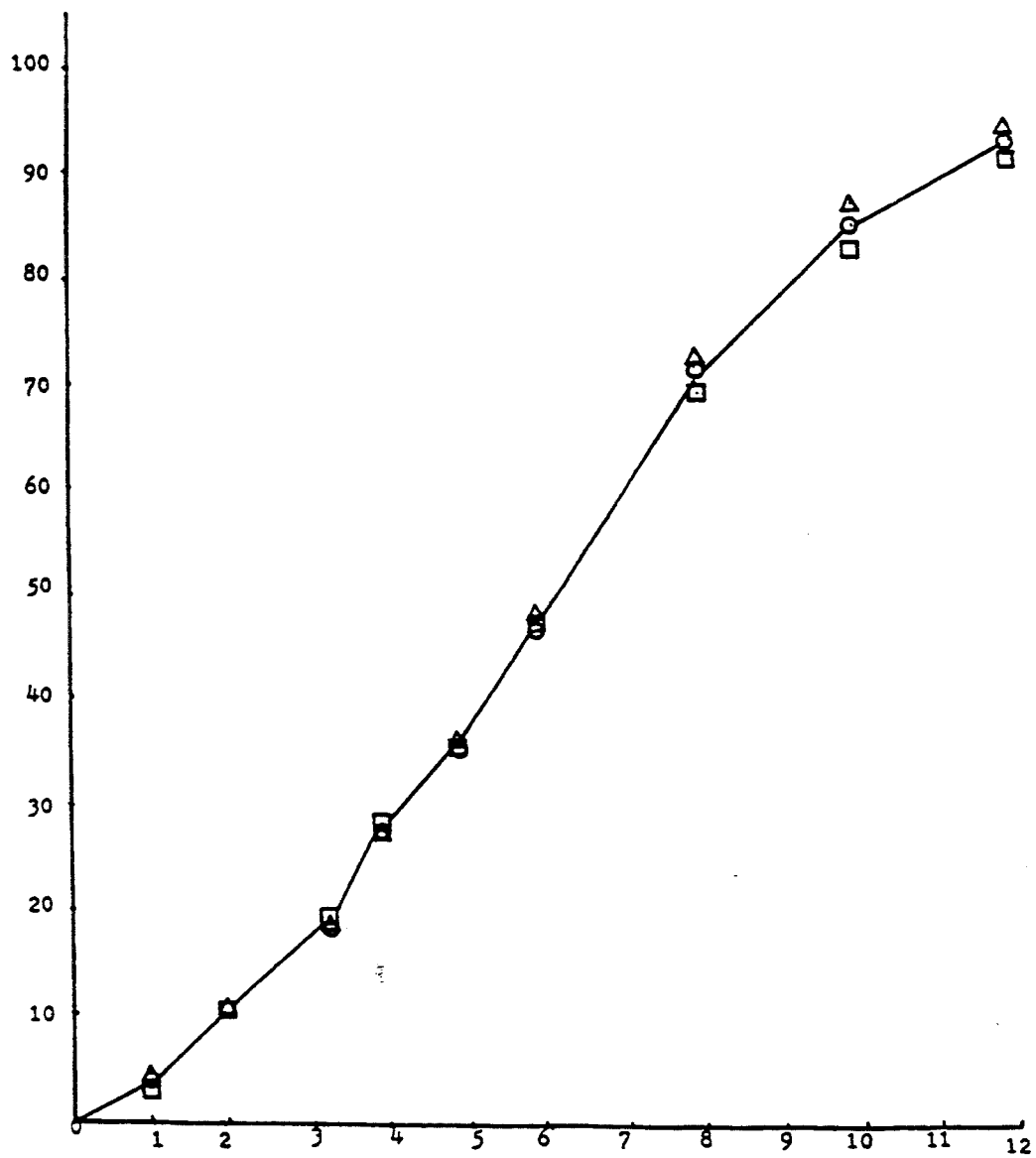
FIG. 2 is a graph which depicts the release of ascorbic acid from beads which have been coated with another embodiment of an aqueous coating composition which was formulated in accordance with the teachings of the present invention. Details concerning the coating composition and the procedures utilized to generate the data which is illustrated can also be found in Example II.
Figure 3:
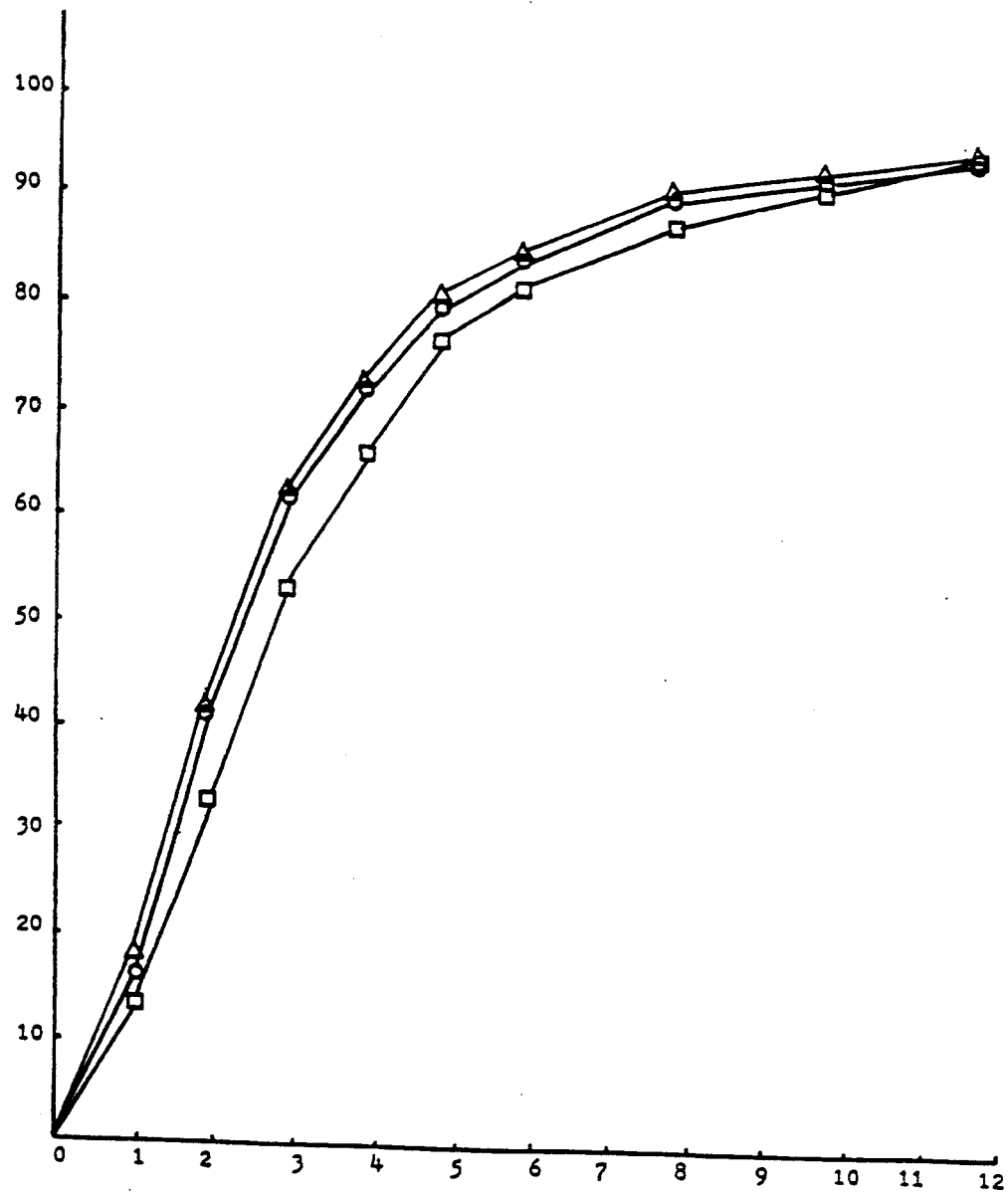
FIG. 3 is a graph which depicts the release of phenylpropanolamine hydrochloride from beads which have been coated with the aqueous coating composition which was employed in the experiment shown in FIG. 2. Details concerning the coating composition and the procedures utilized to generate the data which is illustrated can be found in Example II.
Figure 4:
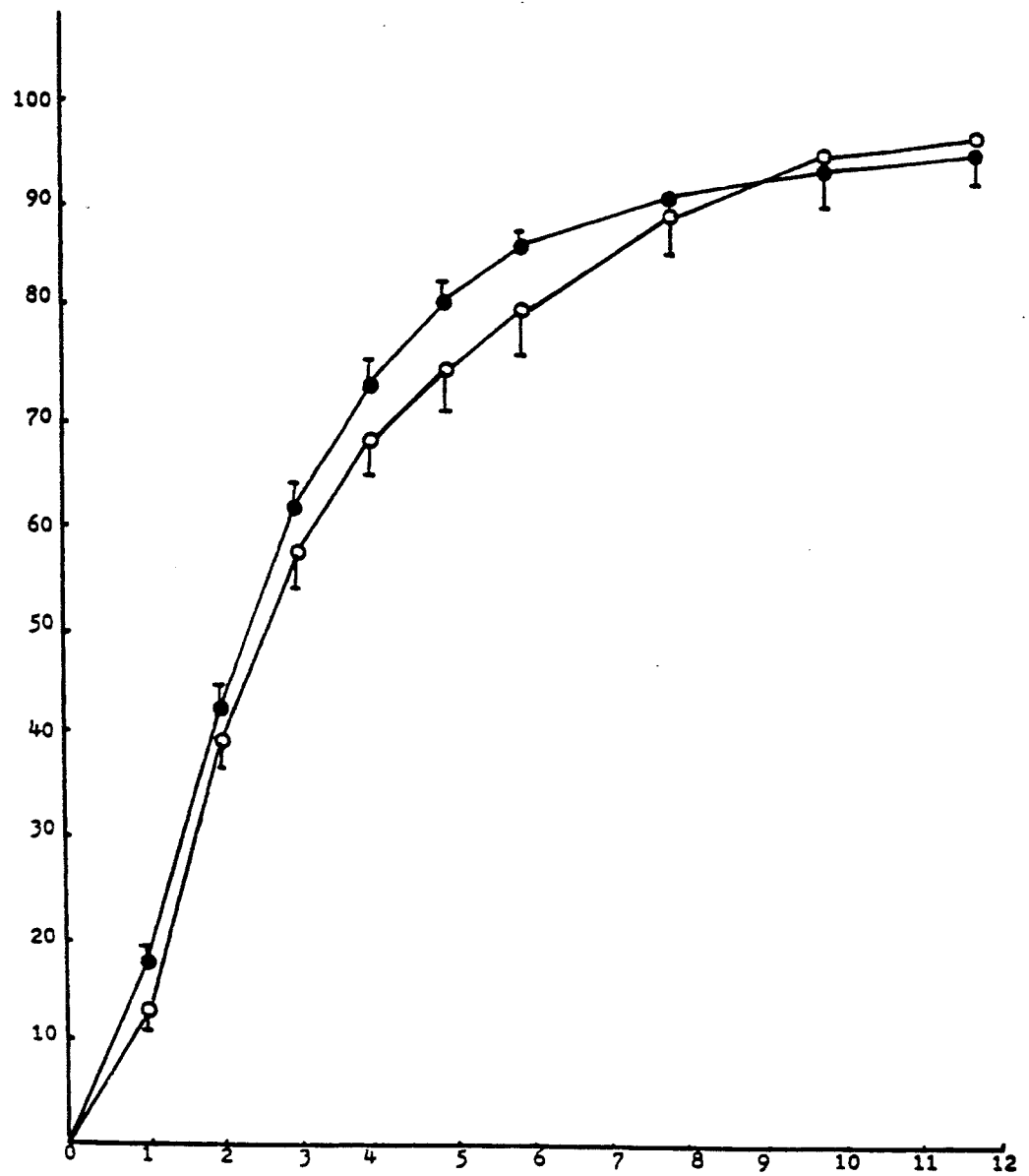
FIG. 4 graphically compares the release of both phenylpropanolamine cation and chloride anion from the coated beads of FIG. 3. Information concerning this work can also be found in Example II.

The results of these analyses are graphically depicted in FIGS. 1-4 wherein FIG. 1 shows ascorbic acid beads coated with Dispersion B in ph buffer at 37° C.; FIG. 2, ascorbic acid beads coated with Dispersion A in ph buffer at 37+ C.; and FIGS. 3 and 4 show phenylpropanol amine hydrochloride beads coated with Dispersion A in deionized water at 37° C. In each of the Figures, the numbers on the vertical axis represent the cumulative percentage of drug released and the numbers on the horizontal axis represent the elapsed time in hours and each point plotted is a mean of two samples. In FIGS. 1, 2, and 3, the circles represent those samples in which the coated beads were dried at room temperature, the triangles represent those samples in which the coated beads were dried at 40° C. for 72 hours, and the squares represent those samples in which the coated beads were dried at 60° C. for 24 hours. Vertical lines where they exist at points on FIG. 1 represent standard deviations. In FIGS. 2 and 3, the standard deviations were too small to include in the graph. In FIG. 4, the graph represented by the solid black circles is based on spectrophotometry assay for the phenylpropanolamine cation and the graph represented by open centered circles is based on the chloride ion selective potentiometry assay. All beads in these plots were dried at room temperature. In this figure, the vertical lines at the plotted points again represent standard deviations. This data demonstrates that the release profiles of the drugs coated with the two elastomeric coatings are markedly zero-order.

EXAMPLE III

Coating 9 of Various Active Substrates

Three coating dispersions were formulated and tested on a number of drug tablets. The coating composition which was utilized employed the polyorganosiloxane latex of Example I which had been blended with colloidal silica (Nalco 1115) to form an aqueous dispersion having a solids content of 35%. The ratio of siloxane latex to colloidal silica in the coating formulations was approximately 4:1 by weight. As illustrated in Table 2, the both the amount and type of water-dispersible organic component was varied in the coating formulations.

The composition and characteristics of core tablets used in this experiment are presented in Table 3. Coating of the dispersion on the tablets was accomplished utilizing a Glatt laboratory coating tower having an inlet temperature of 60°, an air flex setting of 45-95, a flow-rate of 20 meters per minute, an air for pulverization setting of 2 KP/cm$^2$ and a coating time of 45-60 minutes. Between 20 and 34 of the active-ingredient-containing tablets were mixed with ¼" standard concave lactose tablets and the tablet mixture placed in the coating tower. During the coating, the air flop setting was increased to obtain appropriate fluidization of the tablets in the coating chamber. After the coating process had been completed, the coating tablets were fluidized for an additional 5-10 minutes and conditioned by storing them in a 70° C. oven for 72 hours.

Three coated tablets were selected randomly from each coating batch. Each tablet was immersed in 300 ml of a specific dissolution medium contained in a 400 ml water-jacketed beaker maintained at 37°+0.5° C. The dissolution medium was stirred at a constant speed using a floating magnetic stirrer sitting on the bottom of the beaker. Ten-milliliter samples were withdrawn from the beakers and assayed at hourly intervals. The 300 ml volume was kept constant by adding 10 ml of fresh dissolution solvent each time a sample was withdrawn. Samples were diluted with appropriate solvent to a concentration within the spectrophotometric standard curve range. At the end of each experiment each tablet coating was broken in the beaker and the beaker contents were stirred for an additional 10 to 20 minutes to ensure complete dissolution of any undissolved drug. The total amount of drug in each tablet was calculated by adding up the amounts of drug released at each sampling time, including the final sampling after the breaking of the tablet coating. The cumulative percentage of drug released during each time interval was calculated by dividing the amount of drug released during the time interval by the total amount of drug present in the table. The assay method for each drug was:

| | |
|---|---|
| Theophylline and aminophylline | spectrophotometry at 275 nm |
| Salicylic acid | spectrophotometry at 295 nm |
| Amaranth | spectrophotometry at 525 nm |
| Phenylpropanolamine HCl | spectrophotometry at 260 nm |
| Potassium chloride | conductiometry |

Figure 5:
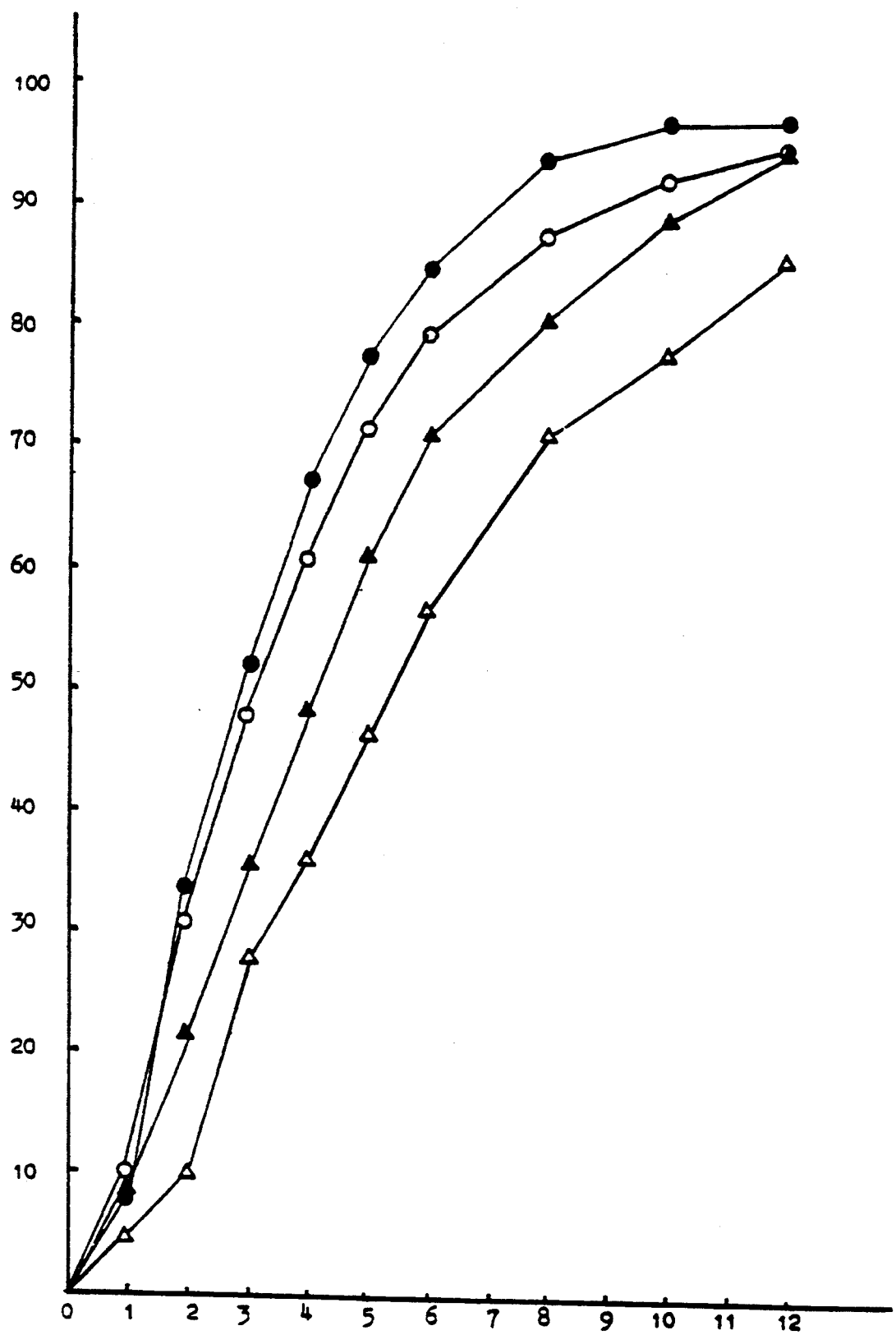
FIG. 5 is a graph which depicts the release of phenylpropanolamine hydrochloride in both acid and mildly basic media from tablets which have been coated with two different aqueous coating composition which have been formulated in accordance with the teachings of the present invention. Details concerning the coating compositions and the procedures utilized to generate the data which is illustrated can be found in Example III.
Figure 6:
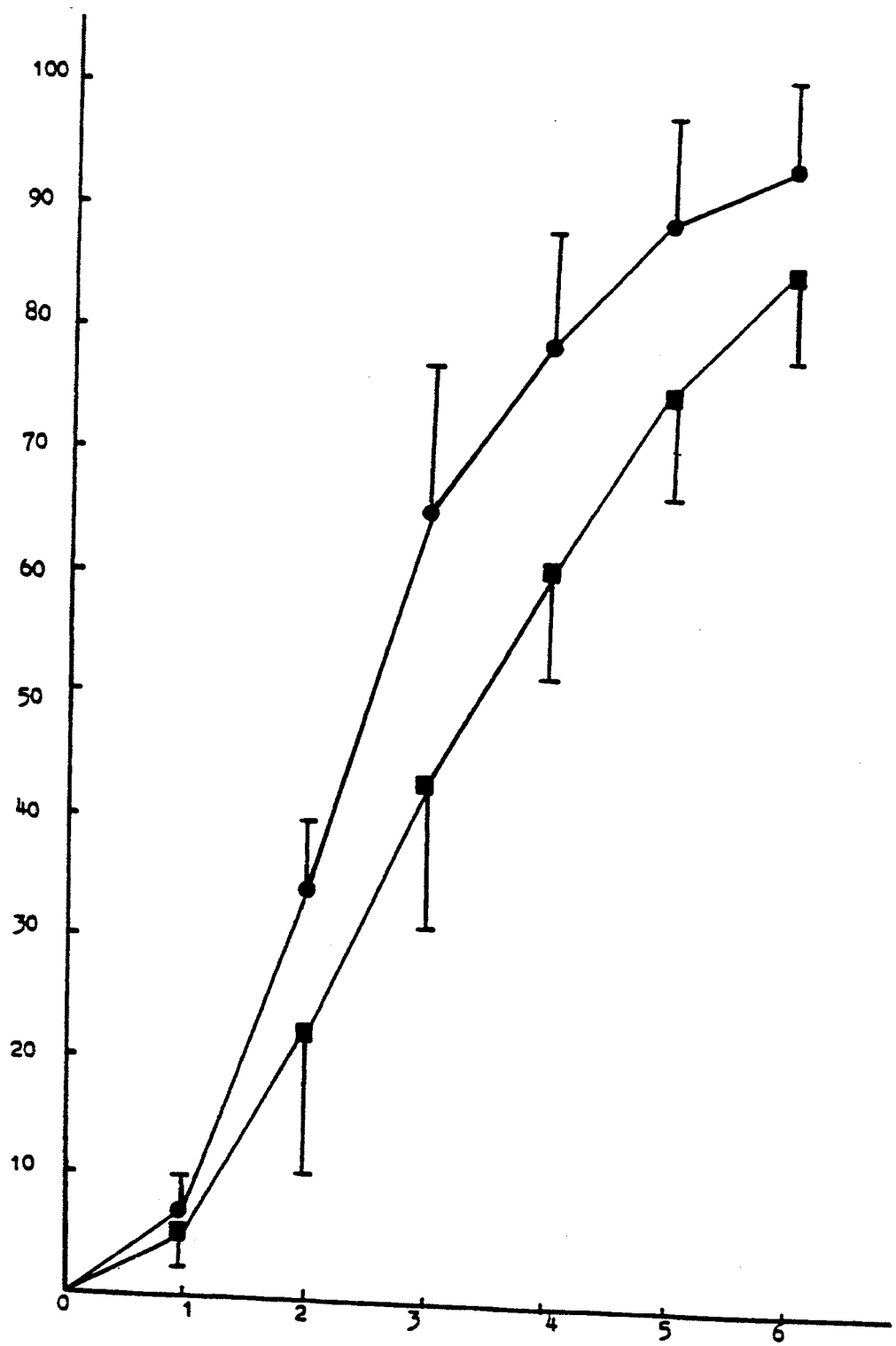
FIG. 6 depicts the release of amaranth from tablets which have been coated with two different aqueous coating compositions which were formulated in accordance with the teachings of the present invention. Details concerning the coating compositions and the procedures utilized to generate the data which is illustrated can be found in Example III.
Figure 7:
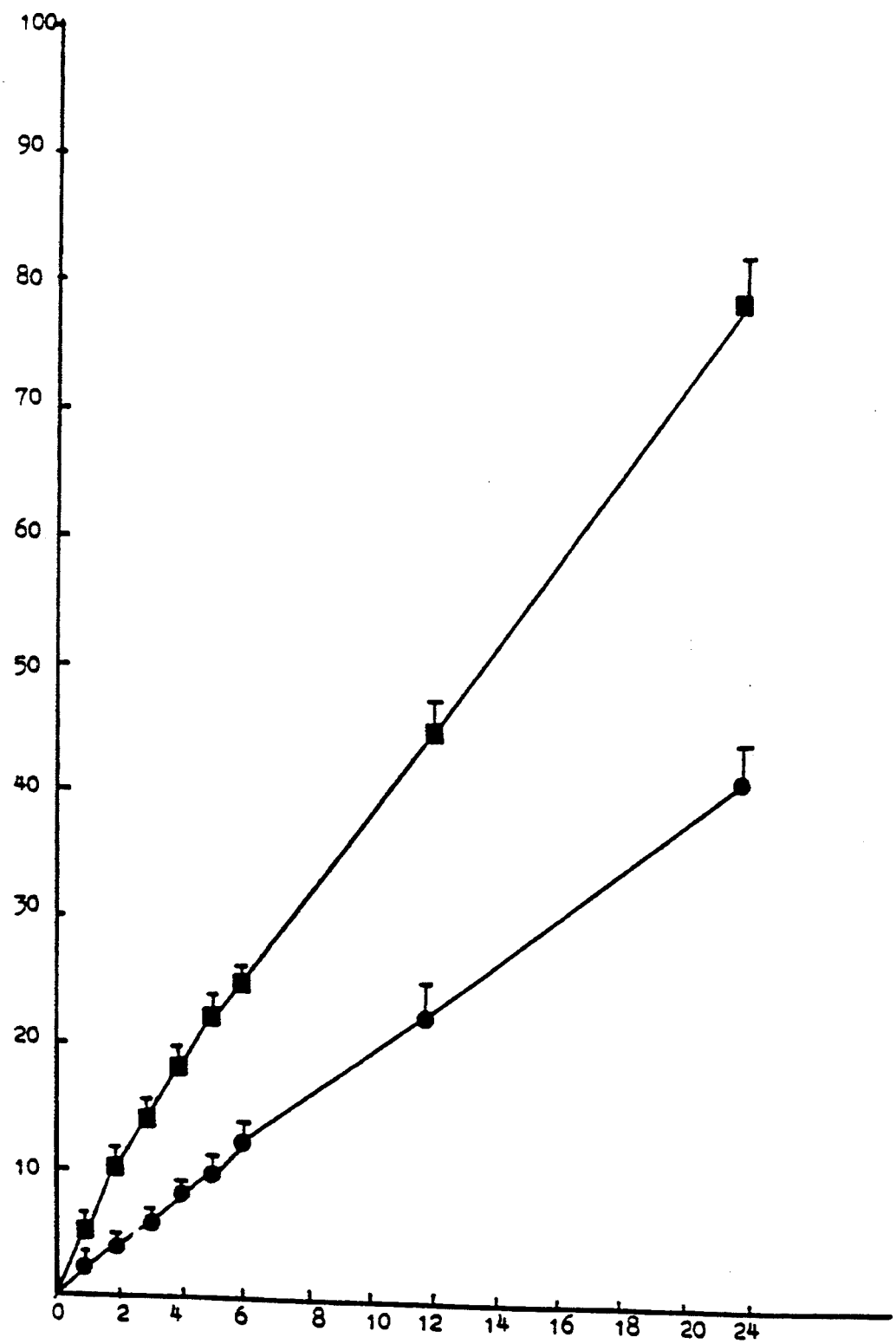
FIG. 7 shows the release of theophylline from tablets which have been coated with an aqueous coating composition which was prepared in accordance with the teachings of the present invention. Details concerning the coating composition and the procedures utilized to generate the data which is illustrated can be found in Example III.

The results of these analysis are set forth in Table 5 and in FIGS. 5-7.

TABLE 2

Composition of Coating-Dispersion.

| Code | Ingredients | Composition Quantity (gm) | Calculated % in dried film |
|---|---|---|---|
| C-2 | Silicone elastomer* dispersion | 400.0 | 70.0 |
| | PEG 400 | 30.0 | 15.0 |
| | PEG 6000 | 30.0 | 15.0 |
| | Deionized water | q.s. 600.0 | |
| C-3 | Silicone elastomer* dispersion | 400.0 | 70.0 |
| | PEG 6000 | 60.0 | 30.0 |
| | Deionized water | q.s. 600.0 | |

TABLE 2-continued

Composition of Coating-Dispersion.

| Code | Ingredients | Quantity (gm) | Calculated % in dried film |
|---|---|---|---|
| C-4 | Silicone elastomer* dispersion | 400.0 | 55.9 |
|  | PEG 400 | 93.3 | 37.3 |
|  | HPMC 7-5** | 12.0 | 4.8 |
|  | PEG 6000 | 2.0 | 0.8 |
|  | PEG 4000 | 3.0 | 1.2 |
|  | Deionized water | q.s. 900.0 | |

*Silicone elastomer dispersion of Example 1 dispersed with Nalco 1116 colloidal silica in a 4:1 ratio (by weight), and having a solids content of 35%.
**Hydroxylpropylmethyl cellulose

TABLE 3

Composition and Characteristics of Core Tablets.

| Tablet | Tablet Code | Principle ingredient and diluent (%) | Binder (%) | Lubricant (%) | Method of preparation | (i) |
|---|---|---|---|---|---|---|
| Amaranth | AM | Amaranth (10%) Lactose (85%) | acacia-gelatin solution q.s. | Talc (5%) | W.G.(a) | 5/1 |
| Phenyl-propanol-amine HCl | PP | Phenyl-propanol-amine HCl (95%) | acacia-gelatin solution q.s. | Talc (5%) | W.G. | 5/16 |
| Amino-phylline | TAM-1 | Amino-phylline, crystalline (95%) | acacia-gelatin solution q.s. | Talc (5%) | W.G. | 5/1 |
| Amino-phylline | TAM-2 | Amino-phylline, crystalline (95%) | acacia-gelatin solution q.s. | Talc (5%) | W.G. | 3/8 |
| Theo-phylline | TH-1 | Theo-phylline, anhydrous (95%) | acacia-gelatin solution q.s. | Talc (5%) | W.G. | 3/8 |
| Theo-phylline | TH-2 | Theo-phylline granules (47.5%)(b) Diapac (47.5%)(c) | — | Talc (5%) | D.T.(d) | 3/ |
| Salicylic acid | SA | Salicylic acid (95%) | acacia-gelatin solution q.s. | Talc (5%) | W.G. | |
| Potassium chloride | KC | Potassium chloride (100%) | — | — | D.T. | 3/8 |

(a)Wet-granulation
(b)Granules from TH-1
(c)Direct compressible sucrose
(d)Direct compression

TABLE 4

Mean Coating Weight and Coating Thickness.

| Code(a) | Mean Coating(b) weight (mg) | Percentage(c) of coating | Mean Coating(d) thickness (microns) |
|---|---|---|---|
| PP-C-2 | 23.6 | 11.8 | 127.8 |
| TH-1-C-2 | 15.6 | 7.2 | 98.2 |
| TAM-1-C-2 | 22.0 | 11.0 | 126.2 |
| AM-C-2 | 29.4 | 11.5 | 136.5 |
| KC-C-3 | 31.6 | 10.0 | 155.0 |
| SA-C-3 | 21.9 | 12.6 | 132.5 |
| AM-C-3 | 25.2 | 12.7 | 138.4 |
| PP-C-3 | 24.6 | 12.4 | 142.0 |
| TAM-2-C-4 | 48.0 | 18.9 | 191.8 |
| TH-1-C-4 | 32.4 | 15.0 | 184.2 |
| TH-2-C-4 | 30.9 | 16.1 | 177.8 |

(a)The initial letters (and numbers) identify the tablet core as set out in Table 3; the C-2, C-3 and C-4 designation refers to the coating dispersion utilized (Table 2).
(b)Mean of 20 or 30 tablets
(c) $\frac{\text{(weight of coated tablets} - \text{weight of uncoated tablets)}}{\text{weight of uncoated tablets}} \times 100$
(d)measured by dividing the difference between the thickness of uncoated and coated tablets by 2.

TABLE 5

Cumulative percentage of phenylpropanolamine HCl released from PP-C-2 and PP-C-3 tablets in 0.1 N HCl and in pH 7.4 phosphate buffer at 37° C. over a 12-hour interval.

| Time (hr) | Tablet PP-C-2 | | Tablet PP-C-3 | |
|---|---|---|---|---|
| | 0.1 N HCl | pH 7.4 buffer | 0.1 N HCl | pH 7.4 buffer |
| 1 | 7.6(a) | 8.2 | 10.2 | 4.7 |
|  | (1.0) | (3.0) | (1.2) | (1.5) |
| 2 | 33.7 | 22.0 | 30.8 | 10.0 |
|  | (3.3) | (4.7) | (3.3) | (2.6) |
| 3 | 52.4 | 35.5 | 48.2 | 27.7 |
|  | (4.5) | (2.5) | (4.8) | (2.7) |
| 4 | 66.9 | 48.5 | 60.9 | 36.2 |
|  | (5.2) | (3.8) | (6.6) | (3.2) |
| 5 | 78.1 | 61.3 | 71.7 | 46.8 |
|  | (5.6) | (3.2) | (6.5) | (2.6) |
| 6 | 85.1 | 71.2 | 79.7 | 57.3 |
|  | (6.0) | (3.4) | (5.6) | (1.7) |
| 8 | 93.6 | 81.4 | 87.9 | 71.2 |
|  | (3.2) | (1.5) | (3.8) | (1.7) |
| 10 | 96.5 | 88.7 | 92.4 | 77.9 |
|  | (2.5) | (0.7) | (3.4) | (2.0) |
| 12 | 97.5 | 95.2 | 95.0 | 86.0 |
|  | (1.0) | (1.2) | (3.0) | (3.6) |

(a)Mean value of 3 tablets, standard deviation in parentheses.

EXAMPLE IV

Effect of Silicone Latex to Colloidal Silica Ratio and Type of PEG

Potassium chloride tablets were coated with the polyorganosiloxane composition of Example I in combination with colloidal silica (Nalco 1116) and polyethylene glycol. Three different silicone latex to silica ratios (2.0, 3.0 and 4.0) and three types of PEG (6000, 4000 and 1540) were utilized in a 3×3 factorial design. The concentration of PEG in the coating was fixed at 30% (w/w) level. The whole design was run in duplicate; hence eighteen batches of coated potassium chloride tablets were prepared in this experiment. For each coating batch, three tablets were randomly chosen and tested for drug release. Data obtained were analyzed using a randomized block design analysis of variance procedure. The results of this experiment are set forth in Table 6.

TABLE 6

Dissolution parameters for potassium chloride coated with various PEG-silicone elastomer dispersions containing three different types of PEG and silicone solid to silica solid ratios. The percent of PEG in each coating is 30% (w/w).

| Replicate | Type of PEG | Silicone/ silica ratio | Release rate (%/hr) | Lag time (hr) | Correlation coefficient |
|---|---|---|---|---|---|
| 1 | | | 14.73 | 0.94 | 0.9980 |
|  | | 2.0 | 14.98 | 0.87 | 0.9987 |
|  | | | 13.97 | 1.00 | 0.9984 |
|  | | | 11.97 | 0.85 | 0.9995 |

TABLE 6-continued

Dissolution parameters for potassium chloride coated with various PEG-silicone elastomer dispersions containing three different types of PEG and silicone solid to silica solid ratios. The percent of PEG in each coating is 30% (w/w).

| Replicate | Type of PEG | Silicone/ silica ratio | Release rate (%/hr) | Lag time (hr) | Correlation coefficient |
|---|---|---|---|---|---|
| | 6000 | 3.0 | 11.97 | 0.93 | 0.9993 |
| | | | 11.74 | 0.95 | 0.9991 |
| | | | 10.87 | 1.47 | 0.9992 |
| | | 4.0 | 10.50 | 1.49 | 0.9997 |
| | | | 11.25 | 1.39 | 0.9992 |
| | | | 12.11 | 0.93 | 0.9994 |
| | | 2.0 | 12.29 | 1.02 | 0.9992 |
| | | | 12.55 | 1.13 | 0.9986 |
| | | | 11.21 | 1.14 | 0.9984 |
| | 4000 | 3.0 | 10.47 | 1.09 | 0.9989 |
| | | | 10.24 | 1.14 | 0.9982 |
| | | | 8.46 | 1.54 | 0.9955 |
| | | 4.0 | 9.72 | 1.88 | 0.9971 |
| | | | 8.58 | 1.79 | 0.9982 |
| | | | 5.70 | 0.05 | 0.9981 |
| | | 2.0 | 6.00 | −0.07 | 0.9980 |
| | | | 6.02 | −0.14 | 0.9981 |
| | | | 3.39 | 0.00 | 0.9954 |
| | 1540 | 3.0 | 3.34 | 0.07 | 0.9958 |
| | | | 3.67 | −0.05 | 0.9961 |
| | | | 2.81 | 1.04 | 0.9996 |
| | | 4.0 | 3.21 | 0.68 | 0.9975 |
| | | | 3.30 | 0.98 | 0.9996 |
| 2 | | | 15.42 | 0.86 | 0.9992 |
| | | 2.0 | 15.11 | 0.96 | 0.9991 |
| | | | 14.16 | 0.85 | 0.9997 |
| | | | 12.35 | 0.84 | 0.9980 |
| | 6000 | 3.0 | 12.76 | 1.02 | 0.9987 |
| | | | 12.78 | 0.83 | 0.9952 |
| | | | 11.47 | 1.35 | 0.9996 |
| | | 4.0 | 10.32 | 1.80 | 0.9992 |
| | | | 10.25 | 1.49 | 0.9999 |
| | | | 12.35 | 0.91 | 0.9994 |
| | | 2.0 | 13.17 | 0.86 | 0.9995 |
| | | | 13.23 | 0.85 | 0.9991 |
| | | | 10.27 | 0.98 | 0.9985 |
| | 4000 | 3.0 | 9.77 | 0.74 | 0.9995 |
| | | | 10.71 | 0.84 | 0.9995 |
| | | | 9.87 | 1.65 | 0.9992 |
| | | 4.0 | 9.38 | 1.50 | 0.9994 |
| | | | 9.78 | 1.54 | 0.9994 |
| | | | 6.26 | −0.03 | 0.9982 |
| | | 2.0 | 5.93 | −0.25 | 0.9988 |
| | | | 5.91 | −0.09 | 0.9993 |
| | | | 4.00 | −0.05 | 0.9958 |
| | 1540 | 3.0 | 3.71 | −0.15 | 0.9986 |
| | | | 3.62 | 0.01 | 0.9986 |
| | | | 3.14 | 1.60 | 0.9971 |
| | | 4.0 | 3.16 | 1.49 | 0.9979 |
| | | | 2.73 | 0.81 | 0.9994 |

In a similar manner, a 3×4 factorial design was employed to investigate the effect of three different types of PEG (6000, 4000 and 1540) and four concentration levels (10.0, 20.0, 30.0 and 40.0) on the drug release characteristics from coated potassium chloride tablets. The silicone latex to silica ratio was fixed at 2.0 to 1.0. The whole experiment was run with two replicates. Data were analyzed using the randomized block design analysis of variance procedure. No drug release was detected with tablets coated with 10% PEG formulations and, therefore, the 4×3 design was reduced to a 3×3 design for data analysis purposes. Data concerning this experiment are contained in Table 7.

TABLE 7

Dissolution parameters for potassium chloride tablets coated with various PEG-silicone elastomer dispersions containing three types of PEG at three different concentration levels. The silicone solid to silica solid ratio is 2.0 to 1.0.

| Replicate | Type of PEG | Percent of PEG in Coating | Release rate (%/hr) | Lag time (hr) | Correlation coefficient |
|---|---|---|---|---|---|
| 1 | | | 40.92 | 0.26 | 0.9990 |
| | | 40.0 | 39.30 | 0.29 | 0.9994 |
| | | | 40.51 | 0.28 | 0.9999 |
| | | | 14.73 | 0.94 | 0.9980 |
| | 6000 | 30.0 | 14.98 | 0.87 | 0.9987 |
| | | | 13.97 | 1.00 | 0.9984 |
| | | | 1.91 | 1.29 | 0.9973 |
| | | 20.0 | 1.88 | 1.31 | 0.9985 |
| | | | 1.84 | 1.26 | 0.9981 |
| | | | 22.75 | 0.34 | 0.9982 |
| | | 40.0 | 23.75 | 0.42 | 0.9994 |
| | | | 20.88 | 0.40 | 0.9990 |
| | | | 12.11 | 0.93 | 0.9994 |
| | 4000 | 30.0 | 12.29 | 1.02 | 0.9992 |
| | | | 12.55 | 1.13 | 0.9990 |
| | | | 2.07 | 1.08 | 0.9969 |
| | | 20.0 | 2.10 | 0.96 | 0.9986 |
| | | | 1.67 | 1.01 | 0.9984 |
| | | | 12.83 | −0.28 | 0.9994 |
| | | 40.0 | 12.48 | −0.29 | 0.9985 |
| | | | 12.53 | −0.36 | 0.9986 |
| | | | 5.70 | 0.05 | 0.9981 |
| | 1540 | 30.0 | 6.00 | −0.07 | 0.9980 |
| | | | 6.02 | −0.14 | 0.9981 |
| | | | 2.11 | 0.68 | 0.9989 |
| | | 20.0 | 2.20 | 0.61 | 0.9999 |
| | | | 2.07 | 0.96 | 0.9996 |

| Replicate | Type of PEG | Silicone/ silica ratio | Release rate (%/hr) | Lag time (hr) | Correlation coefficient |
|---|---|---|---|---|---|
| 2 | | | 40.44 | 0.30 | 0.9998 |
| | | 40.0 | 39.18 | 0.30 | 0.9997 |
| | | | 39.54 | 0.28 | 0.9998 |
| | | | 15.42 | 0.86 | 0.9980 |
| | 6000 | 30.0 | 15.11 | 0.96 | 0.9987 |
| | | | 14.16 | 0.85 | 0.9952 |
| | | | 2.09 | 1.30 | 0.9961 |
| | | 20.0 | 1.97 | 1.49 | 0.9957 |
| | | | 2.11 | 1.26 | 0.9959 |
| | | | 22.60 | 0.38 | 0.9982 |
| | | 40.0 | 21.64 | 0.40 | 0.9986 |
| | | | 23.37 | 0.36 | 0.9990 |
| | | | 12.35 | 0.91 | 0.9994 |
| | 4000 | 30.0 | 13.17 | 0.91 | 0.9995 |
| | | | 13.23 | 0.85 | 0.9991 |
| | | | 1.95 | 1.21 | 0.9988 |
| | | 20.0 | 2.02 | 1.07 | 0.9986 |
| | | | 1.86 | 0.98 | 0.9978 |
| | | | 12.25 | −0.23 | 0.9987 |
| | | 40.0 | 12.56 | −0.44 | 0.9984 |
| | | | 12.55 | −0.28 | 0.9988 |
| | | | 6.26 | −0.03 | 0.9982 |
| | 1540 | 30.0 | 5.93 | −0.25 | 0.9988 |
| | | | 5.91 | −0.09 | 0.9993 |
| | | | 1.94 | 0.74 | 0.9997 |
| | | 20.0 | 2.40 | 0.66 | 0.9997 |
| | | | 2.00 | 0.71 | 0.9950 |

The foregoing data demonstrates that the coated tablets exhibited zero order-release kinetics through the 80% released level. PEG type and silicone latex to silica ratio effects were found with respect to both zero order-release rate and lag times. The data reveals that at a fixed silicone latex to silica ratio, higher molecular weight PEG's enhanced drug release but prolonged the lag times. The data also shows that with a fixed type of PEG, tablets coated with a low silicone latex to silica ratio coating formulation released drug at a faster rate and had a shorter lag time.

EXAMPLE V

Comparison with Uncoated Tablets and Tablets Coated With Dispersions Omitting a Water-Dispersible Organic Component Phenylpropanolamine hydrochloride (PPHCl) and theophylline tablets were coated with silicone coating dispersions formulated in accordance with Example II, but varying the nature and amount of the water-dispersible organic component. Coating weights are shown in Table 8.

TABLE 8

Summary of Drug Release Kinetic Data for Phenylpropanolamine Hydrochloride Tablets and Theophylline Tablets Coated with Modified Silicone Elastomer Dispersions.

| Tablet | Coating Dispersion | Weight of Tablet Coating, milligrams | $K_0$,*** mg drug/hour | R**** |
|---|---|---|---|---|
| 1-PPHCl | 7.5% PEG 400* | 29 | 10 | 0.98 |
| 2-PPHCl | 15% PEG 400 | 37 | 6 | 0.97 |
| 3-PPHCl | 15% PVP** | 40 | 3 | 0.97 |
| 4-PPHCl | 15% PVP | 48 | 2 | 0.90 |
| 5-Theophylline | 7.5% PEG | 33 | 0.5 | 0.97 |
| 6-Theophylline | 15% PEG | 44 | 0.9 | 0.99 |

*Theoretical (W/W) percentage of water-soluble polymer in dry film coating.
**Polyvinylpyrrolidone
***Zero order rate constant.
****Linear correlation coefficient (from linear regression analysis) for kinetic data.

A tablet from each coating set, along with an uncoated PPHCl tablet and an uncoated theophylline tablet, was placed in distilled water maintained at 37° C. and observed hourly to determine whether the coatings remained intact. All tablets coated with the silicone formulation remained intact for at least 24 hours. The two uncoated tablets disintegrated within 1 hour.

Kinetic drug release experiments were conducted on a tablet from each of the five coating sets. A tablet was placed in 300 milliliters of distilled water at 37° C. and the percentage of PPHCl or theophylline that was released was determined from spectrophotometric measurements over a 6–8 hour interval. The data from these experiments are presented in Table 8.

Theophylline and PPHCl tablets were also coated with formulations containing polyorganosiloxane latex and colloidal silica components, but no water-dispersible organic material. So little PPHCl and theophylline was released from tablets coated with these formulations that the data for these coated tablets was not included in the Table.

That which is claimed is:

1. An article comprising a core containing an active agent, said core being completely covered with a continuous cured elastomeric film formed from an aqueous coating composition, said active agent being releasable in a controlled manner through said cured film when the article is placed in a liquid environment, said composition comprising a dispersion of:
   A) polyorganosiloxane latex particles consisting essentially of a cross-linked reaction product of an oil-in-water emulsion of:
      i) 100 parts by weight of a polydiorganosiloxane polymer of the formula $HO(R_2SiO)_xH$;
      ii) 0.5 to 15 parts by weight of an alkoxy silicon compound selected from the group consisting of silanes of the formula $R'_aSi(OR'')_{4-a}$, a partial hydrolyzate of the silane where the partial hydrolyzate is soluble in said polydiorganosiloxane polymer, and mixtures of the silane and partial hydrolyzate; and
      iii) a quantity of anionic surfactant effective to both disperse said polydiorganosiloxane polymer in water and to catalyze the reaction of said alkoxy silicon compound with said polydiorganosiloxane polymer;
   where R is selected from the group consisting of phenyl, vinyl, alkyl, and 3,3,3-trifluoropropyl radicals, R' is a monovalent hydrocarbon radical having up to 12 carbon atoms, R'' is an alkyl radical having 1 to 6, inclusive, carbon atoms, x has an average value in the range of from 3 to 100, inclusive, and a is 0 or 1;
   B) colloidal silica particles present as a dispersed phase in water; and
   C) a water-dispersible, organic material selected from the group consisting of polyvinylpyrrollidone and polyhydric alcohols and esters thereof;
   wherein for each 100 parts by weight of polyorganosiloxane latex particles (A) present in the dispersion, there is present from 5 to 50 parts by weight of colloidal silica (B), and between 8 and 100 parts by weight of water-dispersible material (C),
   and wherein the viscosity of the entire dispersion forming the aqueous coating composition is in a range which permits coating of the coating composition on said active core, and the dispersion forms a continuous, elastomeric film upon removal of the aqueous portion of said mixture and said film is free of any catalysts and other materials which are toxic to animals.

2. The coated article of claim 1 wherein said emulsion of A) is maintained at a temperature of at least 15° C. for at least 5 hours at a pH of less than 5 until said cross-linked reaction product is formed.

3. The coated article of claim 1 where the active agent is bioactive and the liquid environment is the gastro-intestinal tract of an animal.

4. The coated article of claim 3 where the bioactive agent is a drug.

5. The coated article of claim 1 wherein said alkoxysilicon compound is selected from the group consisting of methyltrimethoxy silane, ethyltrimethoxy silane, methyltriethoxy silane, ethyltriethoxy silane, ethylorthosilicate and ethylpolysilicate.

6. The coated article of claim 1 wherein said anionic surfactant is selected from the group consisting of alkyl aryl sulfonic acids and hydrogen alkyl sulfates.

7. The coated article of claim 6 wherein said sulfates are selected from the group consisting of dodecylbenzene sulfonic acid and hydrogen lauryl sulfate.

8. The coated article of claim 1 wherein said polydiorganosiloxane polymer comprises hydroxyl end-blocked polydimethylsiloxane having a viscosity of from about 0.05 Pa to 0.15 Pa at 25° C.

9. The coated article of claim 1 wherein said colloidal silica particles have an average particle size in the range of 4 to 60 nanometers.

10. The coated article of claim 1 wherein said water dispersible organic material is selected from the group consisting of poly(alkylene glycol)s and esters thereof.

11. The coated article of claim 10 wherein said poly(alkylene glycol) comprises a polyethylene glycol having an average molecular weight of from about 400 to about 6,000.

12. The coated article of claim 1 wherein said water dispersible organic material is an oligosaccharide.

13. The coated article of claim 12 wherein said oligosaccharide is selected from the group consisting of sucrose, fructose, and maltodextrins.

14. The coated article of claim 1 wherein R is an alkyl radical selected from the group consisting of methyl, ethyl and propyl radicals.

* * * * *